United States Patent [19]

Horn

[11] Patent Number: 4,743,618
[45] Date of Patent: * May 10, 1988

[54] SUBSTITUTED 2-AMINOTETRALINS

[75] Inventor: Alan S. Horn, Noordhorn, Netherlands

[73] Assignee: Nelson Research & Development Co., Irvine, Calif.

[*] Notice: The portion of the term of this patent subsequent to Jan. 14, 2003 has been disclaimed.

[21] Appl. No.: 891,262

[22] Filed: Jul. 28, 1986

Related U.S. Application Data

[63] Continuation-in-part of Ser. No. 811,768, Dec. 20, 1985, Pat. No. 4,657,925, and a continuation-in-part of Ser. No. 839,976, Mar. 17, 1986, which is a continuation-in-part of Ser. No. 640,685, Aug. 13, 1984, Pat. No. 4,564,628, which is a continuation-in-part of Ser. No. 455,144, Jan. 3, 1983, abandoned, said Ser. No. 811,768, is a continuation-in-part of Ser. No. 640,685, Aug. 13, 1984, Pat. No. 4,564,628, which is a continuation-in-part of Ser. No. 455,144, Jan. 3, 1983, abandoned.

[51] Int. Cl.[4] .................... A61K 31/38; A61K 31/34; C07C 9/06; C07D 211/70

[52] U.S. Cl. ................................... 514/438; 514/357; 514/399; 514/415; 514/427; 514/471; 514/521; 514/523; 546/21; 546/22; 546/329; 546/334; 546/335; 548/111; 548/112; 548/341; 548/412; 548/413; 548/414; 548/503; 548/561; 549/6; 549/74; 549/75; 549/77

[58] Field of Search ................... 558/385, 408; 549/6, 549/216, 218, 222, 74, 75, 77, 492, 494, 495; 546/21, 22, 329, 335; 548/111, 112, 412, 413, 414, 341, 503, 561; 560/138, 139, 110; 564/308; 514/438, 357, 415, 427, 399, 471, 521

[56] References Cited

U.S. PATENT DOCUMENTS

| | | |
|---|---|---|
| 3,930,022 | 12/1975 | Hauck et al. |
| 4,064,271 | 12/1977 | McDermed et al. |
| 4,076,843 | 2/1978 | Hauck et al. |
| 4,267,373 | 5/1981 | Hauck et al. |
| 4,314,082 | 2/1982 | Stout |
| 4,410,519 | 10/1983 | Seiler et al. |
| 4,465,692 | 8/1984 | Horn |
| 4,564,628 | 1/1986 | Horn |

FOREIGN PATENT DOCUMENTS

| | | |
|---|---|---|
| 0026848 | 9/1980 | European Pat. Off. |
| 0041488 | 5/1981 | European Pat. Off. |
| 0064964 | 5/1982 | European Pat. Off. |
| 2333847 | 7/1973 | Fed. Rep. of Germany |
| 2803582 | 1/1978 | Fed. Rep. of Germany |
| 1597140 | 12/1977 | United Kingdom |

OTHER PUBLICATIONS

McDermed John D, McKenzie Gerald M., Phillips Arthur P., (1974) Synthesis and Pharmacology of Some 2-Aminotetralins. Dopamine Receptor Agonists, Journal of Medicinal Chemistry, 1975, vol. 18, No. 4, at pp. 362-367.

Hacksell Uli, Svensson Uno, Nilsson G., Lars J., (1979), N-Alkylated 2-Aminotetralins: Gentral Dopamine-Receptor Stimulating Activity., Journal of Medicinal Chemistry (1979), vol. 22, No. 12 at pp. 1469-1475.

Seiler et al., J. Med. Chem., 1986, 29, at pp. 912-917., Structure-Activity Relationships of Dopaminergic 5-Hydroxy-2-Aminotetralin Derivatives with Functionalized N-Alkyl Substituents.

Beaulieu M. et al., (1984), N,N-Disubstituted 2-Aminotetralins are Potent D-2 Dopamine Receptor Agonists, European Journal of Pharmacolory, 105 (1984) 15-21.

Horn, A. S. et al., (1985) Synthesis and Radioreceptor Binding Activity of N-0437, A New, Extremely Potent and Selective $D_2$ Dopamine Receptor Agonist, Short Communications., Pharmaceutisch Weekblad Scientific Edition, vol. 7, (1985), pp. 208-211.

VanOene Joop C. et al., In Vivo Dopamine Autoreceptor Selectivity Appears to be Critically Dependent Upon the Aromatic Hydroxyl Position in a Series of N,N-Disubstituted 2-Aminotetralins., European Journal of Pharmacology, 102 (1984) pp. 101-115.

Primary Examiner—Alan Siegel
Attorney, Agent, or Firm—Robert J. Baran; June M. Bostich

[57] ABSTRACT

Novel compounds useful as dopamine receptor agonists for the treatment of various diseases of the central nervous system such as Parkinson's disease and related disorders having the structural formula

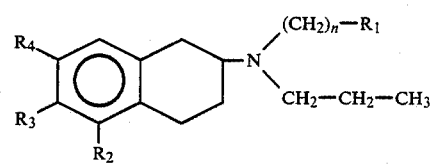

where $R_2$, $R_3$ and $R_4$ are each selected from the group consisting of H, and OA; A is selected from the group consisting of hydrocarbyl radicals;

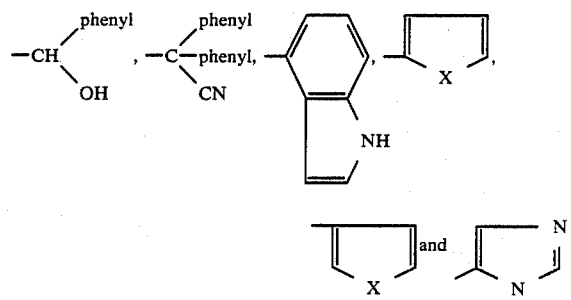

where X is S or O: and pharmaceutically acceptable salts thereof. Also disclosed is a method for inducing a dopaminergic response in a patient by adminstering a pharmacologically-effective amount of one of the foregoing compounds.

10 Claims, No Drawings

SUBSTITUTED 2-AMINOTETRALINS

CROSS REFERENCE TO RELATED APPLICATIONS

This patent application is a continuation-in-part of U.S. patent application Ser. No. 811,768, filed on Dec. 20, 1985, now U.S. Pat. No. 4,657,925 which is a continuation-in-part of U.S. patent application Ser. No. 640,685, filed on Aug. 13, 1984, now U.S. Pat. No. 4,564,628, which is a continuation-in-part of U.S. patent application Ser. No. 455,144, filed Jan. 3, 1983 and now abandoned. This patent application is also a continuation-in-part of U.S. patent application Ser. No. 839,976, which was filed on Mar. 17, 1986, which is a continuation-in-part of U.S. patent application Ser. No. 640,685, filed on Aug. 13, 1984, now U.S. Pat. No. 4,564,628, which is a continuation-in-part of U.S. patent application Ser. No. 455,144, filed Jan. 3, 1983 and now abandoned. All of the above applications were filed in the name of Alan S. Horn and are hereby incorporated by reference.

BACKGROUND OF THE INVENTION

1. Field of the Invention

The invention relates generally to substituted 2-aminotetralins and to processes for preparing such compounds. More particularly, the invention relates to compounds for therapeutic use, in particular in treating disorders of the central nervous, cardiovascular and endocrine systems. The compounds of this invention are also useful for alleviating glaucoma in mammals.

2. Background of the Prior Art

It is known that various hydroxylated 2aminotetralins of the general formula

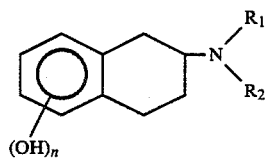

where $R_1$ and $R_2$ are saturated alkyl groups and n is 1 or 2, are dopamine receptor agonists (McDermed et al., J. Med. Chem. 18, 362 (1975); Feenstra et al., Arch. Pharmacol. 313, 213 (1980).

It is also known that certain dopaminergic compounds can lower intraocular pressure in various mammals. For example, it has been suggested that bromocriptine may lower intraocular pressure in man. (See The Lancet, Feb. 4, 1984, "Bromocriptine Eyedrops Lower Intraocular Pressure without Affecting Prolactin Levels.", by Mekki, et al. at pages 287–288.)

Similarly, bromocriptine, as well as lergotrile and pergolide has been shown to lower the intraocular pressure of rabbits and the latter two compounds also lowered the intraocular pressure of monkeys. (see Potter, D. E. and Burke, J. A. (1982/1983), "Effects of Ergoline Derivatives on Intraocular Pressure and Iris Function in Rabbits and Monkeys", Curr. Eye res. 2, 281–288 and Potter, D. E., Burke, J. A. and Chang, F. W. (1984), "Ocular Hypotensive Action of Ergoline Derivatives in Rabbits: Effects of Sympathectomy and Domperidone Pretreatment", Curr. Eye Res. 3, 307–314.)

It has also been shown that certain dopamine analogs of the phenylethylamine class, e.g. N-methyldopamine, N,N-dimethyl-dopamine and N,N-di-n-propyldopamine, may alter ocular function by operating through a variety of mechanisms. However, N-methyl dopamine appeared to function by suppressing aqueous humor formation. (See Potter, D. E., Burke, J. A. and Chang, F. W. (1984), "Alteration in Ocular Function Induced by Phenylethylamine Analogs of Dopamine", Curr. Eye Res. 3, 851–859.)

Finally, certain aminotetralins were shown to lower intraocular pressure in rabbits. (See Burke, J. A., Chang., F. W. and Potter, D. E. (1984), "Effects of Aminotetralins on Intraocular Pressure and Pupillary Function in Rabbits", J. Auton, Pharmacol. 4, 185–192.)

SUMMARY OF THE INVENTION

There has now been discovered certain novel compounds having the structural formula

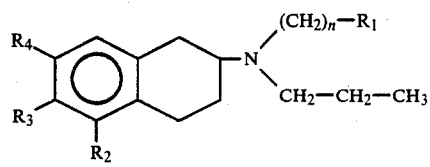

where $R_2$, $R_3$ and $R_4$ are each selected from the group consisting of H and OA; A selected from the group consisting of hydrocarbyl radicals, preferably having from 1 to 12 carbon atoms, e.g. phenyl or lower alkyl radicals, i.e. methyl, ethyl, propyl, etc.; n is 2 or 3; and $R_1$ is selected from the group consisting of 3-hydroxyphenyl, 4-hydroxphenyl, 3-pyridyl, 4-pyridyl,

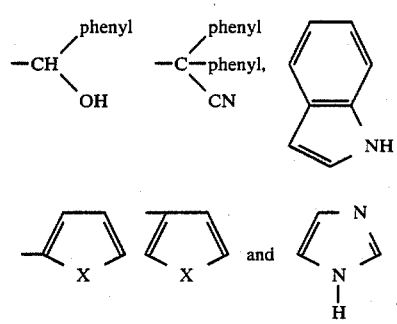

With the proviso that at least one of $R_2$, $R_3$ and $R_4$ is H, and at least one of $R_2$, $R_3$ and $R_4$ is not H and $R_2$ and $R_4$ are not both OA and pharmaceutically-acceptable salts thereof. Preferably $R_1$ is selected from the group consisting of 3-pyridyl, 4-pyridyl,

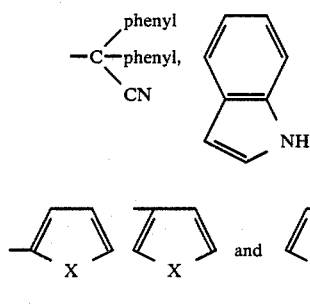

The above radicals may also be further substituted with various groups. In particular, such substituents may be selected from the group consisting of hydroxy, nitro, azido, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, e.g. from 1 to 5 carbon atoms, i.e. from 1 to 3 carbon atoms. X is oxygen or sulfur preferably, the abbove radicals are not further substituted. The most preferred radicals for $R_1$ are 2-thienyl and 3-thienyl. In the compounds of the present invention, at least one of $R_2$, $R_3$ and $R_4$ is H, and at least one of $R_2$, $R_3$ and $R_4$ is not H, and $R_2$ and $R_4$ are not both OA.

These compounds are useful as dopamine agonists and, in particular, dopamine D-2 receptor agonists for the treatment of disorders of the central nervous, cardiovascular and endocrine systems such as Parkinson's disease and related disorders, hypertension and hyperprolactinemia. In particular, the compounds of this invention are useful in the treatment of glaucoma in mammals.

Thus, the ether compounds of this invention may be used in a manner similar to the phenols, catechols and acylated derivatives thereof disclosed in the above-cited patents and patent applications. Being ethers, however, it is expected that said compounds, in use, are slower-acting but would continue to show activity over a greater period of time than said phenols, catechols and acylated derivatives.

DETAILED DESCRIPTION OF THE INVENTION

The above compounds may be made by disclosed in the patent applications cited above and incorporated by reference herein.

Specific preferred compounds, which are within the scope of the above general formula include:

2-(N-n-propyl-N-2-[2-thienyl]ethylamino)-5-methoxytetralin.
2-(N-n-propyl-N-2-[2-thienyl]ethylamino)-5-phenoxytetralin.
2-(N-n-propyl-N-2-[2-thienyl]ethylammino)-5-n-propoxytetralin.
2-(N-n-propyl-N-2-[3-thienyl]ethylamino)-5-methoxytetralin.
2-(N-n-propyl-N-2-[3-pyridyl]ethylamino)-5-methoxytetralin.
2-(N-n-propyl-N-2-[4-pyridyl]ethylamino)-5-methoxytetralin.
2-(N-n-propyl-N-2-[3-hydroxyphenyl]ethylamino-5-methoxytetralin.
2-(N-n-propyl-N-2-[1-hydroxy-1-phenylmethyl]ethylamino-5-methoxytetralin.
2-(N-n-propyl-N-2-[1,1-diphenyl-1-cyanomethyl]ethylamino-5-methoxytetralin.
2-(N-n-propyl-N-2-[2-furanyl]ethylamino-5-methoxytetralin.

A preferred embodiment of this invention is a method of treatment which comprises inducing a dopaminergic response by administering a therapeutically effective amount of one of the foregoing compounds to a patient. In general, a pharmacologically effective daily dose can be from 0.01 mg/kg to 100 mg/kg per day, and preferably from about 0.1 mg/kg to 25 mg/kg per day, bearing in mind, of course, that in selecting the appropriate dosage in any specific case, consideration must be given to the patient's weight, general health, metabolism, age and other factors which influence response to the drug. A particularly preferred dose is 1.0 mg/kg per day.

Another embodiment of this invention is the provision of pharmaceutical compositions in dosage unit form which comprise from about 2 mg. to 500 mg. of a compound of the above formula.

The pharmaceutical composition may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate, or sodium phosphate; granulating and disintegrating agents, for example maize starch, or alginic acid; binding agent, for example starch, gelatine, or acacia; and lubricating agents, for example magnesium stearate, stearic acids, or talc. The tablets may be uncoated or they may be coated by known techniques to delay disintegration and adsorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate, or kaolin, or as soft gelatine capsules wherein the active ingredient is mixed with an oil medium, for example arachis oil, liquid paraffin, or olive oil.

Aqueous suspensions contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum trangacanth, and gum acacia; dispersing or wetting agents may be a naturally-occurring phosphatide, for example lecithin, or condensation products of an alkylene oxide with fatty acids, for example of polyoxethylene stearate, or condensation products of ethylene oxide with long chain aliphatic alcohols, for example heptadecaethyleneoxycetanol, or condensation products of ethylene oxide with partial esters derived from fatty acids and a hexitol, for example, polyoxyethylene sorbitol monooleate, or condensation product of ethylene oxide with partial esters derived from fatty acids and hexitol anhydrides, for example polyoxyethylene sorbitan monooleate. The said aqueous suspensions may also contain one or more preservatives, for example ethyl, n-propyl, or p-hydroxy benzoate, one or more coloring agents, one or more flavoring agents, and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, may also be present.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol.

The pharmaceutical compositions may be tableted or otherwise formulated so that for every 100 parts by weight of the composition there are present between 5 and 95 parts by weight of the active ingredient. The dosage unit form will generally contain between about 1 mg. and about 100 mg. of the active ingredient of the formula stated above.

From the foregoing formulation discussion it is apparent that the compositions of this invention can be administered orally or parenterally. The term parenteral as used herein includes subcutaneous injection, intraveneous, intramuscular, or intrasternal injection or fusion techniques.

Even more preferably, the method of the present invention comprises administering the above-described compounds to the eye of a mammal to reduce intraocular pressure. Moreover, the levo (−) isomers of these substituted compounds are believed to be the more active isomers for use in the method of the present invention.

Suitable ophthalmic carriers are known to those skilled in the art and all such conventional carriers may be employed in the present invention. Thus, a particular carrier may take the form of a sterile ophthalmic cointment, cream, gel, solution, or dispersion and preferably a solution. Also including as suitable ophthalmic carriers are slow releasing polymers, e.g. "Ocusert" polymers, "Hydron" polymers, etc. Stabilizers may also be used as, for example, chelating agents,, e.g. EDTA. Anti-oxidants may also be used, e.g. sodium bisulfite, sodium thiosulfite, 8-hydroxy quinoline or ascorbic acid. Sterility typically will be maintained by conventional ophthalmic preservatives, e.g. chlorbutanol, benzalkonium chloride, cetylpyridinium chloride, phenyl mercuric salts, thimerosal, phenethyl alcohol, etc., for aqueous formulations, and used in amounts which are nontoxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable ophthalmic carriers or stabilizers include sterile, substantially isotonic, aqueous solutions containing minor amouns, i.e., less than about 5% by weight hydroxypropylmethylcellulose, polyvinyl alcohol, carboxymethylcellulose, hydroxyethylcellulose, glycerine, EDTA, sodium bisulfite and ascorbic acid.

The amount of active compound to be used in the therapeutic treatment of glaucoma will vary with the age of the patient and the severity of the glaucoma. Generally, a dose level of one or two drops of the foregoing aqueous solution 1–4 times daily would be a suitable dosage amount. Generally, the concentration of active compound will vary between about 0.01 and about 5% and preferably between about 0.05 and about 1% (wt./v calculated on the basis of the free base) of said ophthalmic composition.

Preferably, the ophthalmic composition of this invention should have a pH within the range of about 4.0 to 9.0 when intended for topical application. Above and below this pH range the solution may irritate and sting the eye of the user. The solutions of the present invention may be maintianed between about pH 4.0 and 7.5 with suitable amounts of buffering agents including borate, carbonate, phosphate. Tris (hydroxymethyl aminomethane), acetate and citrate buffers.

A preferred ophthalmic composition is a preserved aqueous solution containing the following ingredients at approximately the indicated concentration.

TABLE

| | |
|---|---|
| Active compound | 0.001–1 wt. % |
| Stabilizer | 0.01–0.1 wt. % |
| Preservative | 0.005–0.5 wt. % |
| Buffer (sufficient to maintain pH between about 4.0 and 7.5) | 0.1–0.001 M |
| NaCl qs. ad. | (isotonic) |
| Water qs. ad. | 100% |

To illustrate the manner in which the invention may be carried out, the following examples are given. It is understood, however, that the examples are for the purpose of illustration and the invention is not to be regarded as limited to any of the specific materials or conditions therein.

EXAMPLE

Male, albino New Zealand rabbits and female *Cebus apella* monkeys are used in the example. Rabbits are used primarily to screen for undue ocular toxicity of 2-(N-propyl-N-2-phenylethylamino)-5-methoxytetralin (active compound) before conducting experiments in monkeys.

A racemic mixture of 2-(N-propyl-N-2-phenylethylamino)-5-methoxytetralin (active compound) is dissolved in distilled water (vehicle or carrier) on the day of the experiment. Solutions are admiistered in a masked manner, that is, solutions are prepared by a person that was neither involved in drug administration nor mesurement of intraocular pressure (IOP) and pupil diameter (PD). The solution of the active compound is applied unilaterally with the contralateral (fellow) eye receiving vehicle only. Five monkeys are treated bilaterally with vehicle; one to two vehicle-treated monkeys are included each time a different dose of the active compound is used. Doses of active compound tested are: 0.165, 0.5 and 1.65 mg.

After taking two baseline (0 time) measurements, aliquots (50 $\mu$l ) of the solution of active compound and/or vehicle, only, ar administered topically. Subsequently, IOP measurements are made at 0.5, 1, 2, 3, 4 and 5 hours post drug. The active compound is found to effectively lower the intraocular pressure of the monkey are compared to the vehicle, alone.

While particular embodiments of the invention have been described it will be understood of course that the invention is not limited thereto since many obvious modifications can be made and it is intended to include with this invention any such modifications as will fall within the scope of the appended claims.

What is claimed is:

1. Optically active or racemic compounds having the general formula

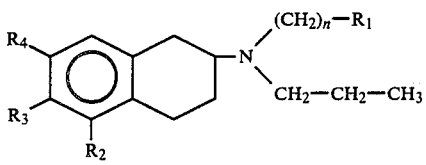

wherein $R_2$, $R_3$ and $R_4$ are each selected from the group consisting of H and OA; A is selected from the group consisting of hydrocarbyl radicals, n is 2 or 3 and $R_1$ is selected from the group of radicals consisting of 3-pyridyl,

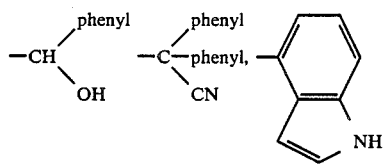

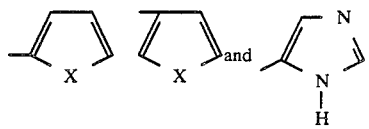

and further substituted derivatives thereof wherein the substituents are selected from the group consisting of hydroxy, nitro, azido, sulfate, sulfamido, halogen, hydrocarbyl and hydrocarbyl radicals, wherein said hydrocarbyl radicals are substituted with atoms selected from the group consisting of halogen, nitrogen, oxygen and sulfur and phosphorus and said hydrocarbyl radicals comprise from 1 to 12 carbon atoms, wherein X is oxygen or sulfur, and wherein at least one of $R_2$, $R_3$ and $R_4$ is H and at least one of $R_2$, $R_3$ and $R_4$ is not H, and $R_2$ and $R_4$ are not both OA and pharmaceutically acceptable salts thereof.

2. The compound of claim 1 wherein said radicals are not further substituted.

3. The compound of claim 2 wherein A is selected from the group consisting of phenyl and alkyl radicals having from 1 to 12 carbon atoms.

4. The compound of claim 2 wherein A is selected from alkyl radicals having from 1 to 3 carbon atoms.

5. The compound of claim 2 wherein $R_1$ is 2-thienyl or 3-thienyl.

6. The compound of claim 5 wherein $R_3$ and $R_4$ are hydrogen.

7. The compound of claim 6 wherein $R_2$ is methyl.

8. A composition for reducing the intraocular pressure in mammals which comprises an effective amount of the compound of claim 1 and an ophthalmic carrier for said compound.

9. A method for reducing the intraocular pressure in mammals which comprises administering an effective amount of the compound of claim 1.

10. A method comprising:
inducing a dopaminergic response in a patient by administering a pharmacologically-effective amount of the compound of claim 1.

* * * * *